United States Patent
Metz et al.

(10) Patent No.: US 6,673,056 B2
(45) Date of Patent: Jan. 6, 2004

(54) SNAP-IN INSERT FOR CONVEX OSTOMY FACEPLATE

(75) Inventors: Michael A. Metz, Chicago, IL (US); Walter F. Leise, Jr., Lindenhurst, IL (US); Ernest J. Wicker, Island Lake, IL (US)

(73) Assignee: Hollister Incorporated, Libertyville, IL (US)

( * ) Notice: Subject to any disclaimer, the term of this patent is extended or adjusted under 35 U.S.C. 154(b) by 86 days.

(21) Appl. No.: 10/008,037

(22) Filed: Nov. 5, 2001

(65) Prior Publication Data

US 2003/0088219 A1 May 8, 2003

(51) Int. Cl.[7] .................................................. A61F 5/44
(52) U.S. Cl. ...................................... 604/338; 604/332
(58) Field of Search ................................. 604/332–345

(56) References Cited

U.S. PATENT DOCUMENTS

| | | | |
|---|---|---|---|
| 4,219,023 A | 8/1980 | Galindo | |
| 4,781,708 A | 11/1988 | Steer | |
| 4,834,731 A | * 5/1989 | Nowak et al. | 604/339 |
| 4,889,534 A | 12/1989 | Mohiuddin et al. | |
| 5,004,464 A | 4/1991 | Leise, Jr. | |
| 5,163,930 A | 11/1992 | Blum | |
| 5,429,625 A | 7/1995 | Holmberg | |
| 5,501,678 A | 3/1996 | Olsen | |
| 5,607,413 A | 3/1997 | Holmberg et al. | |
| 5,693,036 A | 12/1997 | Kilgour | |
| 5,718,696 A | 2/1998 | Kollerup | |
| 5,730,735 A | 3/1998 | Holmberg | |
| 5,730,736 A | * 3/1998 | Sawers et al. | 604/344 |
| 5,947,941 A | 9/1999 | Leise, Jr. et al. | |
| 6,210,384 B1 | 4/2001 | Cline | |

FOREIGN PATENT DOCUMENTS

| | | |
|---|---|---|
| EP | 0 415 282 A1 | 3/1991 |
| EP | 0 479 573 B1 | 4/1992 |
| FR | 2 721 204 A | 12/1995 |
| WO | WO 93 04646 A | 8/1992 |
| WO | WO 93 18725 A | 9/1993 |

* cited by examiner

*Primary Examiner*—Dennis Ruhl
*Assistant Examiner*—Linh Truong
(74) *Attorney, Agent, or Firm*—Marshall, Gerstein & Borun LLP

(57) ABSTRACT

A snap-in insert is disclosed for use with the faceplate of an ostomy appliance. The faceplate includes a convex pressure ring and an adhesive barrier pad or wafer that extends over the convex surface of that ring. The insert has an apertured support wall that is flexible but sufficiently stiff to support and thereby brace the barrier pad about the faceplate's stoma-receiving opening.

18 Claims, 2 Drawing Sheets

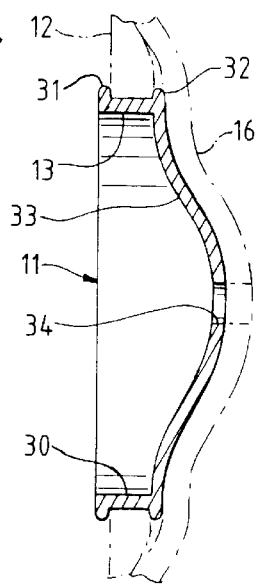
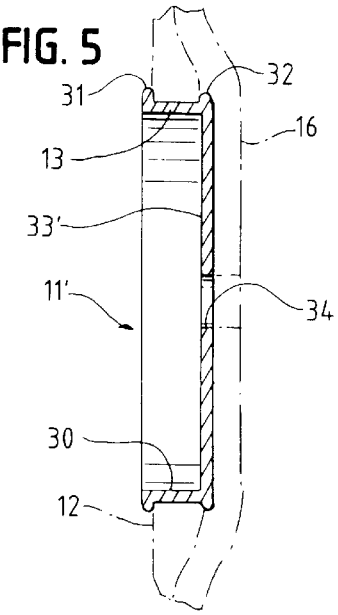
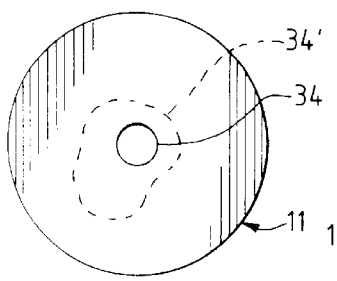
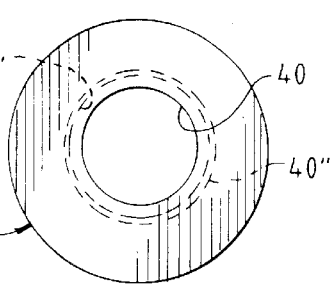
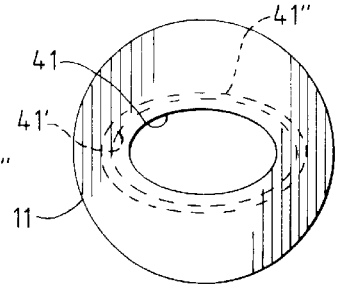

SNAP-IN INSERT FOR CONVEX OSTOMY FACEPLATE

BACKGROUND AND SUMMARY OF THE INVENTION

U.S. Pat. No. 4,834,731 (Nowak et al.) discloses an ostomy appliance having a relatively rigid convex pressure ring for causing stomal protrusion for patients with flush or recessed stomas, thereby aiding in the discharge of effluent directly into a collection pouch and helping to prolong the effectiveness of the adhesive seal between a faceplate and peristomal skin surfaces. It has also been known to provide such a faceplate with a rigid convex pressure ring having an inside diameter substantially larger than a patient's stoma and with an adhesive skin barrier pad or wafer that covers the convex surface and extends inwardly over the opening of the pressure ring, with the adhesive pad having a small starter opening so that, with the use of scissors, a patient or caregiver may easy enlarge and shape the opening in the pad to match the outline of the patient's stoma. Such a faceplate is commonly referred to as a "cut-to-fit" faceplate, meaning that the opening in the adhesive area layer may be sized and shaped at the time of application to meet a patient's needs. A downside is that such a faceplate construction requires the rigid convex pressure ring to have an opening substantially larger then a patient's stoma in order to allow enlargement and shaping of the starter opening in the adhesive pad, thereby reducing the effectiveness of the convex ring in producing stomal protrusion.

Rigid convex pressure rings in the form of adapters for the purpose of converting planar faceplates into convexly-curved faceplates are also known. Reference may be had to U.S. Pat. No. 5,429,625 (Holmberg), U.S. Pat. No. 4,219,023 (Galindo), U.S. Pat. No. 5,163,930 (Blum), U.S. Pat. No. 5,004,464 (Leise), and U.S. Pat. No. 6,210,384 (B1) (Cline). International Publication WO 93/04646 (Olsen) also discloses such an adapter.

SUMMARY OF THE INVENTION

This invention is concerned with a convex faceplate, particularly one of the cut-to-fit type, and a snap-in insert for such a faceplate. The insert supports and thereby braces the portion of the adhesive barrier pad that extends over or across the opening of the convex pressure ring. If desired, the insert may itself provide a convexly-curved support wall for substantially increasing the convexity of the faceplate to which the insert is attached.

The support wall of the insert is provided with an opening which may be pre-sized and shaped during manufacture to approximate any of various sizes and shapes of patient's stomas. Such a pre-formed opening may, by way of example, be circular or oval in shape, it being recognized that a substantial portion of patients have stomas generally oval-shaped in outline. Alternatively, the opening in the support wall of the insert may constitute a starter opening that may then be enlarged and shaped with scissors by a user or caregiver to match the outline of a patient's stoma. In either case, the insert, after being snapped into place within the opening of a faceplate's convex pressure ring, may be rotated within that opening to ensure proper orientation of the insert in relation to that patient's stoma.

Briefly, the insert is formed from a stiff but nevertheless flexible and shaped-recoverable polymeric material and has a cylindrical rim and an apertured bodyside support wall. The rim has a pair of axially-spaced outwardly-projecting annular retention ribs sized and positioned to engage the bodyside and pouchside surfaces of the rigid pressure ring of a convex faceplate. The ribs therefore lock the insert against axial movement relative to the convex pressure ring while at the same time allowing relative rotation of the parts. The support wall of the insert is apertured with the aperture serving either as a starter opening, which may then be enlarged and shaped with scissors, or as a pre-formed opening that is cut during manufacture to approximate any of a number of stoma sizes and shapes. In one embodiment of the invention, the thin, flexible support wall is convexly curved to supplement or increase the convexity already provided by the rigid pressure ring of the faceplate, whereas in another embodiment the support wall of the insert is generally planar.

Other features, advantages, and objects of the invention will become apparent from the specification and drawings.

DRAWINGS

FIG. 4 is an enlarged sectional view of the insert illustrating its effect in reforming and bracing the barrier pad of an ostomy faceplate (depicted in phantom).

FIG. 5 is a sectional view of a snap-in insert constituting a second embodiment of this invention.

FIGS. 6–7 are bodyside elevational views of inserts having apertures of different sizes and shapes.

DETAILED DESCRIPTION OF PREFERRED EMBODIMENTS

Figure 1:
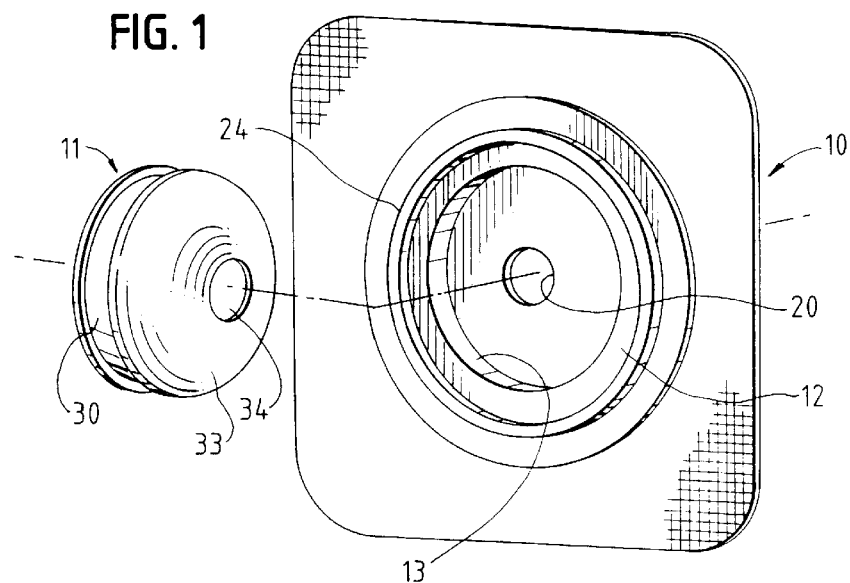
FIG. 1 is a perspective view of an ostomy faceplate and an insert attachable thereto.
Figure 2:
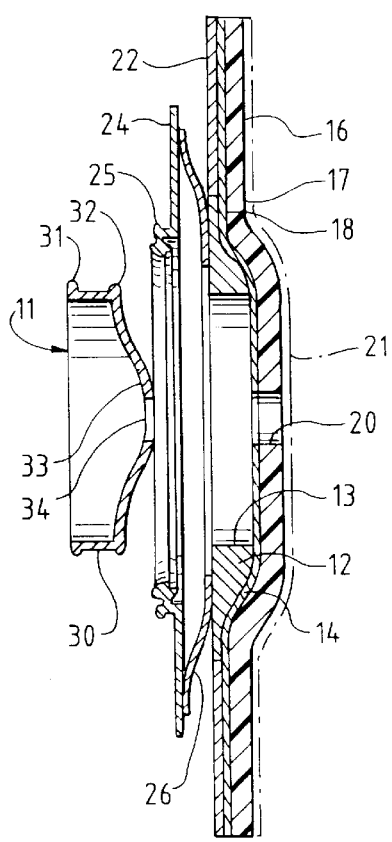
FIG. 2 is a vertical sectional view of the faceplate and insert in separated condition.

Referring to FIGS. 1 and 2, the numeral 10 generally designates an adhesive convex faceplate for a two-piece ostomy appliance of a type known in the art. Such a faceplate is currently made and sold by Hollister Incorporated, Libertyville, Ill., and is shown here simply as an example of the type of faceplate with which snap-in insert 11 may be used. It is to be understood that non-critical features of the faceplate 10 may be changed or eliminated without affecting the essential relationships between the parts. For instance, faceplate 10 is shown and described as one component of a two-piece ostomy appliance, the other component being an ostomy pouch (not shown) that is designed to be coupled to and uncoupled from the faceplate as needed; however, the faceplate might instead be permanently attached to a pouch in what is commonly known as a one-piece appliance. In the latter case, the pouch would be required to be a drainable one, having a drain opening large enough to allow entry of insert 11 into the interior of the pouch for attachment to the faceplate as hereinafter described.

The faceplate 10 is characterized by having a relatively rigid convex pressure ring 12 with a large and generally cylindrical opening 13. As shown most clearly in FIG. 3, the pressure ring has a convexly curved bodyside surface 14 and a generally planar pouchside surface 15. Covering the bodyside surface is an adhesive pad or wafer 16 which has a skinfriendly adhesive layer 17 and a flexible backing layer 18 of a suitable polymeric film. The film may be secured to the bodyside surface of the convex pressure ring by any suitable means; in the illustration given, a layer of hot melt adhesive 19 performs that function. As depicted in FIG. 2, the adhesive pad follows the contour of the pressure ring's bodyside surface and extends radially inwardly in planar fashion over the stoma-receiving cylindrical opening 13 of the convex pressure ring. A small starter opening or aperture 20 is centrally located in the pad, such opening being concentric with the opening 13 of the convex pressure ring. Aperture 20 serves as a starter opening into which the tip of a scissors may be inserted for purposes of enlarging and shaping the opening to match the outline of a patient's stoma.

Adhesive layer 17 may be composed of any adhesive suitable for attaching the faceplate to the peristomal skin surfaces of a patient. A conventional acrylic adhesive may be used although hydrogel and hydrocolloid adhesives are preferred because of their skinfriendly character. A conventional hydrocolloid adhesive, commonly known as a skin barrier adhesive, is believed to be particularly effective because it has both wet and dry tack and contains hydrocolloids capable of absorbing fluids and swelling as they do so. The hydrocolloid particles, which may consist of carboxymethylcellulose, pectin, gelatin, or any other of a variety of hydrocolloids and superabsorbents known for use in skin barrier formulation, are dispersed in a soft, pliant elastomeric adhesive material such as, for example, polyisobutylene. For further information concerning such skin barrier adhesives, reference may be had to co-owned patents U.S. Pat. No. 5,492,943 (Stempel) and U.S. Pat. No. 5,935,363 (Gilman), the disclosures of which are incorporated by reference herein.

The bodyside surface of the adhesive layer or pad 16 may be covered by a protective release sheet 21 of any suitable material such as, for example, a siliconized paper or plastic film that may be easily stripped away from the adhesive when the faceplate is to be attached to a patient's skin. Also, if desired, the pouchside surface of pad 16 may, if desired, be covered by a soft layer of non-woven fabric 22 adhesively attached to backing film 18.

FIGS. 1 and 2 illustrate a preferred means for attaching the faceplate to an ostomy pouch (not shown), but other attaching means may be provided as already indicated. In the construction illustrated, a plastic flange or coupling ring 24 is provided with a coupling portion 25 capable of mating with another coupling ring provided by a collection pouch or bag (not shown). An annular web 26 of thin, flexible thermoplastic material has its inner periphery heat sealed at 27 to the pouchside surface 15 of pressure ring 12 and its outer periphery heat sealed or otherwise permanently connected to flange 24. The web allows limited floating movement of the flange 24 and also permits a user to insert his/her fingers between flange 24 and pad 16 to facilitate attachment of the faceplate and pouch coupling rings. For further information concerning the structure and operation of the coupling and the advantages of the floating flange feature, reference may be had to U.S. Pat. No. 5,185,008 (Lavender) and U.S. Pat. No. 5,947,941 (Leise et al.), the disclosures of which are incorporated herein.

Insert 11 includes a generally cylindrical rim 30 having a pair of axially-spaced outwardly projecting retention ribs 31 and 32. A support wall 33 with a central aperture 34 is formed integrally with the rim and, in the embodiment shown in FIGS. 1–4, is convexly curved in a bodyside direction. The insert is formed from a stiff but nevertheless flexible and shape-recoverable polymeric material such as, for example, polyethylene or polypropylene, it being understood that other polymeric materials having similar properties are known and may be used.

The distance between ribs 31 and 32 is the same or slightly greater than the axial dimension of cylindrical opening 13 of convex pressure ring 12, and the outside diameter of each rib is slightly greater than the diameter of opening 13. The remainder of the outside diameter of rim 30 is the same or slightly less than the diameter of opening 13 and, because of the limited flexibility and shape-recoverability of the insert, the insert may be easily forced by finger pressure into the mounted position depicted in FIG. 3 with retention ribs 31 and 32 bearing against surfaces 15 and 14 and locking the insert against axial movement relative to the convex pressure ring. Because both the opening 13 of the pressure ring 12 and the rim 30 of the insert 11 are cylindrical in shape, the insert may then be rotated into any selected angular position within the opening of the pressure ring.

Referring to FIG. 4, the convex curvature of the insert's support wall 33 causes the adhesive pad 16 of the faceplate to bulge outwardly in a bodyside direction, thereby substantially increasing the convexity of the faceplate as a whole. It has been found that an insert having a convex curvature as illustrated in FIGS. 1–4 may increase the convexity of the faceplate by as much as two or more times. If a lesser degree of convexity is desired, then the curvature of support wall 33 may be made less than that shown, and if the original convexity of the faceplate is believed sufficient, then insert 11' as shown as FIG. 5 may be used instead of the insert 11 of FIGS. 1–4. Insert 11' is identical to insert 11 except that its support wall 33' is planar rather than convex. In both cases, the support wall braces that portion of the adhesive pad within the limits of opening 13 of convex pressure ring 12 and helps that portion resist inward displacement when the product is in use.

Figure 3:
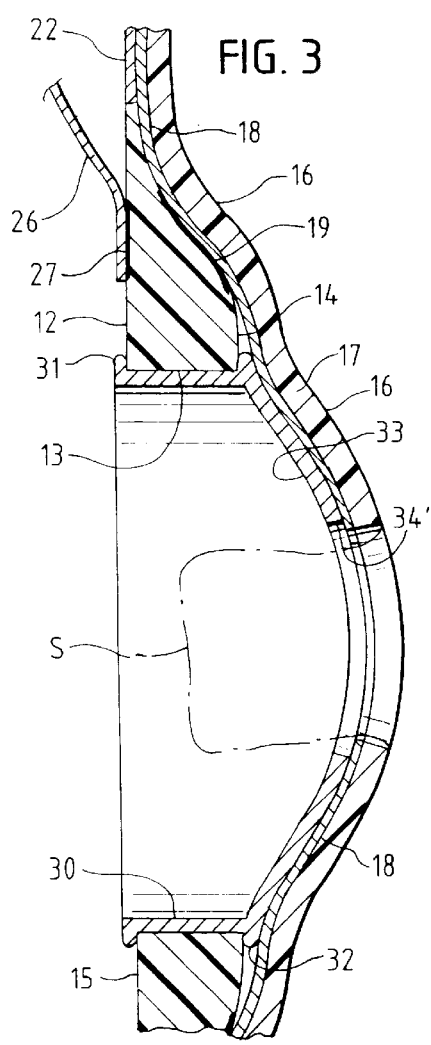
FIG. 3 is a an enlarged sectional view similar to FIG. 2 but showing the insert and faceplate in attached condition.

In use of the combination, the starter opening 20 of faceplate 10 is first cut to match the size and shape of a user's stoma. An insert element 11 selected to meet a user's needs is then fitted into place within the opening of the convex pressure ring 30. The insert may, for example, have a small starter opening 34 as shown in FIGS. 1, 2, and 4–6 and, in that case, the starter opening is enlarged by cutting wall 33 with scissors to form an enlarged opening 34' that generally matches the shape and size of the stomas, although preferably slightly larger than the reformed opening in adhesive pad 16 (FIG. 3). The stoma may therefore protrude into the interior of the collection pouch, or at least into insert 11, as shown in phantom in FIG. 3, without directly contacting the edges of the enlarged opening 34' formed in wall 33 of the insert. To ensure proper orientation of the insert relative to the stoma, the insert may be rotated within the faceplate as already indicated.

Instead of being provided with a cut-to-fit starter opening 34, the insert may be of a type having a pre-formed opening that approximates the size and shape of a patient's stoma. FIG. 7 illustrates an insert 11 having a support wall with a large circular opening 40, and other inserts having even larger pre-formed openings 40' and 40" may also be provided for selection by users. Alternatively, as shown in FIG. 8, a user may select an insert 11 having an opening 41 of oval shape, which may also be made available in larger sizes 41' and 41", again, to approximate the size and shape of a user's stoma.

While in the foregoing we have disclosed embodiments of the invention in considerable detail for purposes of illustration, it will be understood that many of those details may be varied without departing from the spirit and scope of the invention.

What is claimed is:

1. A snap-in insert for the faceplate of an ostomy appliance wherein the faceplate includes a rigid pressure ring having a generally cylindrical stoma-receiving opening of predetermined diameter, a convexly-curved bodyside surface, and a generally planar pouchside surface; said insert being formed from a stiff but flexible and shape-recoverable plastic material and having a cylindrical rim and an apertured bodyside support wall; said rim having a pair of axially-spaced outwardly-projecting retention ribs sized and positioned to engage the bodyside and pouchside surfaces of a faceplate ring about the stoma receiving opening thereof for securing said insert therein; one of said retention ribs being engageable with said bodyside surface of said pressure ring having an outside diameter sufficiently greater than said predetermined diameter to allow said one rib to be inserted axially through said stoma-receiving opening and thereafter to flex outwardly into engagement with said bodyside surface.

2. The insert of claim 1 in which said apertured support wall of said insert is generally planar.

3. The insert of claim 2 in which said aperture of said support wall is generally circular.

4. The insert of claim 2 in which said aperture of said support wall is generally oval.

5. Claim 5 the insert of claim 2 in which said aperture constitutes a starter opening and said bedside support wall is scissors-cutable for enlarging and shaping said aperture to match the size and outline of a patient's stoma.

6. The insert of claim 1 in which said support wall is convexly curved in a bedside direction.

7. The insert of claim 6 in which said aperture of said support wall is generally circular.

8. The insert of claim 6 in which said aperture of said support wall is generally oval.

9. The insert of claim 6 in which said aperture constitutes a starter opening and said bedside support wall is scissors-cutable for enlarging and shaping said aperture to match the size and outline of a patient's stoma.

10. In combination, an ostomy appliance faceplate including a rigid pressure ring having a generally cylindrical stoma-receiving opening, a convexly curved bedside surface, and a generally planar pouchside surface; a soft, deformable adhesive pad covering said bedside surface and having an apertured central portion extending over said opening of said pressure ring; and an insert received in said opening; said insert having a generally cylindrical rim and a pair of axially-spaced outwardly-projecting retention ribs each of a diameter larger than said opening and engaging said bedside and pouchside surfaces of said pressure ring about said opening thereof; said insert including an apertured support wall engaging and supporting said apertured central portion of said adhesive pad.

11. The combination of claim 10 in which said apertured support wall of said insert is generally planar.

12. The combination of claim 11 in which said aperture of said support wall is generally circular.

13. The combination of claim 11 in which said aperture of said support wall is generally oval.

14. The combination of claim 11 in which said aperture of said support wall constitutes a starter opening, said support wall being scissors-cutable for enlarging and shaping said aperture to match the size and outline of a patient's stoma.

15. The combination of claim 11 in which said apertured support wall of said insert is convexly curved in a bedside direction.

16. The combination of claim 15 in which said aperture of said support wall is generally circular.

17. The combination of claim 11 in which said aperture of said support wall is generally oval.

18. The combination of claim 11 in which said aperture of said support wall constitutes a starter opening, and said support wall is scissors-cutable for enlarging and shaping said aperture of said support wall to match the size and outline of a patient's stoma.

* * * * *

UNITED STATES PATENT AND TRADEMARK OFFICE
CERTIFICATE OF CORRECTION

PATENT NO.   : 6,673,056 B2
DATED        : January 6, 2004
INVENTOR(S)  : Michael A. Metz et al.

It is certified that error appears in the above-identified patent and that said Letters Patent is hereby corrected as shown below:

<u>Column 2,</u>
Line 32, "FIGS. 6-7" should read -- FIGS. 6-8 --.

<u>Column 5,</u>
Lines 26, 31 and 36, "bedside" should read -- bodyside --;

<u>Column 6,</u>
Lines 3, 5, 8 and 26, "bedside" should read -- bodyside --.

Signed and Sealed this

Eighteenth Day of May, 2004

JON W. DUDAS
*Acting Director of the United States Patent and Trademark Office*